(12) United States Patent
Srinivas et al.

(10) Patent No.: US 9,221,749 B2
(45) Date of Patent: Dec. 29, 2015

(54) PROCESS FOR PRODUCING AMIDE COMPOUNDS

(71) Applicant: COUNCIL OF SCIENTIFIC & INDUSTRIAL RESEARCH, New Delhi (IN)

(72) Inventors: Darbha Srinivas, Maharashtra (IN); Anuj Kumar, Maharashtra (IN); Nepak Devadutta, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/382,366

(22) PCT Filed: Mar. 4, 2013

(86) PCT No.: PCT/IN2013/000127
§ 371 (c)(1),
(2) Date: Sep. 2, 2014

(87) PCT Pub. No.: WO2013/128477
PCT Pub. Date: Sep. 6, 2013

(65) Prior Publication Data
US 2015/0099900 A1    Apr. 9, 2015

(30) Foreign Application Priority Data

Mar. 2, 2012 (IN) .............................. 602/DEL/2012

(51) Int. Cl.
*C07C 231/10* (2006.01)
(52) U.S. Cl.
CPC .................................... *C07C 231/10* (2013.01)
(58) Field of Classification Search
CPC .................................................. C07C 231/10
See application file for complete search history.

(56) References Cited

U.S. PATENT DOCUMENTS 6,043,061 A    3/2000  Ishii et al.

FOREIGN PATENT DOCUMENTS

EP    1 266 962 A2    12/2002
EP    1 835 033 A1    9/2007

OTHER PUBLICATIONS

International Search Report dated Aug. 7, 2013 for Application No. PCT/IN2013/000127.
Chemical Abstracts, vol. 75, 1971, abstract No. 129306g.
Gunanathan, C., et al., "Direct Synthesis of Amides from Alcohols and Amines with Liberation of $H_2$", Science, vol. 317, Aug. 10, 2007, pp. 790-792.
Ghosh, S.C., et al, "Simple $RuCl_3$-Catalyzed Amide Synthesis from Alcohols and Amines", Eur. J. Org. Chem., 2010, pp. 4266-4270.
Kim, J. W., et al., "Heterogeneously Catalyzed Efficient Oxygenation of Primary Amines to Amides by a Supported Ruthenium Hydroxide Catalyst", Angew. Chem. Int. Ed., vol. 47, 2008, pp. 9249-9251.
Wang, Y., et al., "Manganese oxide-catalyzed transformation of primary amines to primary amides through the sequence of oxidative dehydrogenation and successive hydration", Chem. Commun., vol. 48, 2012, pp. 2642-2644.
Xu, W., et al., "Copper-Catalyzed Aerobic Oxidative Synthesis of Primary Amides from (Aryl)methanamines", Synlett, vol. 23, 2012, pp. 801-804.

*Primary Examiner* — Shailendra Kumar
(74) *Attorney, Agent, or Firm* — Ladas & Parry LLP

(57) ABSTRACT

An efficient and eco-friendly process for producing amide compounds comprising contacting a primary amine with molecular oxygen-containing gas, solvent and ammonia solution in the presence of a non-precious metal-containing ordered, mesoporous solid catalyst is disclosed.

11 Claims, No Drawings

PROCESS FOR PRODUCING AMIDE COMPOUNDS

RELATED APPLICATION INFORMATION this application is a 371 of International Appplication PCT/IN2013/000127 filed 4 Mar. 2013 entitled "Process For Producing Amide Compounds", which was published in the English language on 6 Sep. 2013, with International Publication Number WO2013/128477 A1 and which claims priority from Indian Patent Application Number 602/DEL/2012 filed 2 Mar. 2012, the consent which is incorporated herein by reference.

FIELD OF THE INVENTION

The present invention relates to a process for producing amide compounds in the presence of a non-precious metal-containing ordered, mesoporous solid catalyst.

More particularly, the present invention relates to an efficient and eco-friendly process for producing amide compounds comprising contacting a primary amine with molecular oxygen-containing gas and ammonia solution in the presence of a non-precious metal-containing ordered, mesoporous solid catalyst.

BACKGROUND OF THE INVENTION

Amides are important class of organic compounds used in the manufacture of drugs, engineering plastics, detergents and lubricants. (Meth)acrylamide and caprolactum are two amide group-containing monomeric compounds of great industrial relevance in the preparation of polymers. Compounds of amides are known to have excellent anthropod-controlling activity and application in the treatment of HIV disease.

Although there have been several methods to prepare amides, their preparation under neutral conditions without generating waste by-products is a challenging task. Amides are mostly prepared by the reaction of amines with activated acid derivatives (acid chlorides and anhydrides) (Chemical Abstracts, Vol. 75, 1971, abstract no. 129306g). This reaction generates equimolar quantity of acid by-product which needs further processing steps to neutralize and separate from the desired amide product. Further, this reaction becomes sluggish and often fails to take place if the amine is deactivated due to presence of electron, withdrawing substituents in it.

Amide compounds have also been produced at an industrial scale by hydrating the corresponding nitrile at high temperatures over a reduced metal catalyst—Raney Ni and Cu, for example. In recent times, nitrile hydratase-containing microorganisms are also being used in their production (U.S. Pat. No. 6,043,061; EP 1,266,962 A2; EP 1,835,033A1).

There have been some reports on the direct synthesis of amides from alcohols and amines in the presence of metal catalysts (Gunanathan et al., Science, Year 2007, Vol. 317, pp. 790 792; S. C. Ghosh and S. H. Hong, Eur. J. Org. Chem. Year 2010, pp. 4266-4270). Primary amines are directly acylated by equimolar amounts of alcohols to produce amides and molecular hydrogen (the only product) in high yields and high turnover numbers. This reaction is catalyzed by a homogeneous catalyst, ruthenium complex based on a dearomatized PNN-type ligand [where PNN is 2-(di-tert-butylphosphinomethyl)-6-(diethylaminomethyl)pyridine]. No base or acid promoters are required. However, there is a requirement of additional reagent alcohol to produce amides.

Oxygenation of amines is an efficient route for amides synthesis. This transformation possibly proceeds by a tandom process of oxidative dehydrogenation of amines to nitriles, followed by hydration to produce corresponding amides. Kim et al (Angew. Chem. Int. Ed., Year 2008, Vol. 47, pp. 9249-9251) reported the application of alumina-supported ruthenium hydroxide for this transformation. Ruthenium, a precious metal, is a less abundant and expensive metal and hence, is not desirable for use. Wang et al. (Chem. Commun., Year 2012, DOI: 10.1039/c2cc17499e) demonstrated the use of manganese oxide octahedral molecular sieves (OMS-2) catalysts for this reaction. Low hydrothermal stability and durability are the issues with this catalyst. Further, OMS-2 is a microporous catalyst with pore size of 4 to 5 Å. Bulkier amines are, therefore, not amenable for transformation to amides over these prior-art catalysts. Water, a by-product generated during the amide formation reaction deactivates and destabilizes the catalyst. Although, 87% yield of benzylaminde is obtained over fresh catalyst in its first, on reuse the yield of amide dropped down to 82% which is a clear indication of less stability of OMS catalysts during long term usage.

In view of importance of amide compounds in industrial applications and drawbacks of prior-art processes which include use of expensive, low abundant metals, mineral acids or bases for rearrangements, low structural stability and microporosity of catalysts, etc., it is desirable to have a more efficient catalyst process.

Metal-containing porous solid catalysts, especially those of mesoporous silicas, silicates, aluminophosphates and silico-aluminophosphates have been known for their catalytic activity in other organic transformations. These catalysts are known for their high thermal, hydrothermal and mechanical stability during their thick porewalls (20-40 Å). The inventors disclose herein a novel invention wherein ordered, mesoporous non-precious metal-containing catalysts are used for the preparation of amides from amines.

OBJECTIVES OF THE INVENTION

The main objective of present invention is to provide an efficient and eco-friendly process for producing amide compounds in the presence of a non-precious metal-containing ordered, mesoporous solid catalyst.

Another object of present invention is to provide a catalytic process for producing amides wherein the catalyst is stable, rugged and reusable for reactions in the presence of water.

Another object of present invention is to provide an acid/acid chloride and aldehyde-free process for the preparation of amide compounds.

SUMMARY OF THE INVENTION

Accordingly, the present invention provides a process for producing amide compounds from a primary amine with more than 95% conversion, wherein said process comprises the steps of:
  a. contacting a primary amine, solvent and ammonia solution with a non-precious metal-containing ordered, mesoporous, solid catalyst, wherein the amount of catalyst ranges from 10 to 40% by weight of amine, solvent ranges from 10 to 30 times by weight of said primary amine and ammonia solution ranges from 2 to 10 times by weight of amine;
  b. pressurizing the reactor with molecular oxygen-containing gas at a pressure of 2 to 6 bar;

c. subjecting the reaction mixture obtained in step (b) to a temperature in the range of 100 to 160° C. and for a reaction period of 3 to 8 hrs to obtain said amide compound, and, d. separating the amide compound from the left out ammonia solution, solvent and catalyst.

In one embodiment of the present invention the non-precious metal-containing mesoporous solid catalyst used in step (a) comprises a third-row transition metal selected from manganese, iron, vanadium, chromium and copper and an ordered, mesoporous catalyst selected from the group of mesoporous silicas, silicates, aluminophosphates and silicoaluminophosphate.

In an embodiment of the present invention the ordered, mesoporous catalyst has an average pore size ranging from 25 to 60 Å, pore wall thickness ranging from 40 to 110 Å and specific surface area ranging from 500 to 1000 $m^2/g$.

In another embodiment of the present invention molecular oxygen-containing gas used in step (b) is air or pure oxygen.

In another embodiment of the present invention solvent used in step (a) is selected from the group of 1,4-dioxane, tetrahydrofuran and dimethyl sulphoxide.

In yet another embodiment of the present invention conversion of amine is 100%.

In another embodiment of the present invention the selectivity towards amide compounds, preferably amide and imine is greater than 80% by weight.

In another embodiment of the present invention, solid catalyst has an ordered mesoporous structure with an average pore size ranging from 25 to 60 Å, pore wall thickness ranging from 40 to 110 Å and specific surface area ranging from 500 to 1000 $m^2/g$.

In yet another embodiment of the present invention, the solid catalyst is stable and reusable.

In still another embodiment of the present invention, the reaction can be conducted in a batch, semi-batch or continuous fixed-bed reaction mode.

In still yet another embodiment, when the process is conducted in a continuous fixed-bed mode the catalyst is shaped into pellets or extrudates and used.

In still another embodiment of the present invention, the process is carried out optionally in the absence of ammonia.

In still another embodiment of the present invention, the process is carried out optionally in the presence of water.

DETAILED DESCRIPTION OF THE INVENTION

In the investigations leading to present invention, it was found that the non-precious metal-containing mesoporous solid catalysts of the present invention are highly efficient and could be easily separated from the products for further reuse. The prior art catalysts are expensive, less abundant or less stable. A highly stable and easily separable catalyst system e.g., the catalyst of the present invention is more advantageous.

The catalyst of the present invention is efficient even at moderate temperature and oxygen pressure. Near complete conversion of amine and high selectivity of amide compound are obtained.

It is a feature of the process of present invention that the catalyst is a solid and the reaction takes place in a heterogeneous condition. The solid catalyst can be easily separated from products by centrifugation-filtration/decantation for further reuse.

It is another feature of the process of present invention that the-process is eco-friendly, economical and generates no waste products unlike in the prior art processes.

It is the unique feature of the catalyst of present invention that they are highly stable in the aqueous medium.

Another unique feature of the present invention is that its mesoporous structure enables easy access of active sites to the reactant molecules and enables high conversions. Further, the diffusion of reactant and product molecules is higher than that of prior-art catalysts.

Yet another unique feature of the present invention is that the catalyst of the present invention is selective for producing amide but not for breakage of C—N bond of amine.

Still another feature is that amide formation occurs even by water instead of ammonia solution.

Still another feature is that amide formation occurs even by water instead of ammonia solution. Metal-containing mesoporous framework structures of the catalysts of present invention are highly active and selective for the transformation of amines to amides at moderate reaction temperature and pressure. They avoid all the drawbacks of the prior-art catalyst processes. The process using them is more efficient, since the catalyst is used in the mesoporous form. The process of the present invention is eco-friendly as it does not generate by-product inorganic salt formed as a consequence of neutralization steps. Further, the process of the present invention is economical as less expensive and durable catalysts are being employed and as it is possible for the catalytic process to be conducted in a continuous-flow mode.

The novelty in the invention arises from the fact that the reaction has been achieved with excellent conversions using non-precious metals on an ordered mesoporous scaffold. The use of non-precious metals will ensure a more cost effective process while the ordered mesoporous scaffold provides an industrially more feasible platform with better diffusion properties and stability. Previous reports have not been able to show a cost-effective, industrially viable and robust system for carrying out the said reaction.

The present invention is illustrated herein below with examples, which are illustrative only and should not be construed to limit the scope of the present invention in any manner.

EXAMPLES

The catalyst was prepared by the known procedure (Journal of Porous Materials, Vol. 18 (Issue No. 3), Year 2010, pp. 369-378)

Example 1

This example illustrates the preparation of manganese containing three-dimensional, cubic, mesoporous silica catalyst Mn-SBA-16 with Si/Mn molar ratio=40. In a typical synthesis of Mn-SBA-16 (Si/Mn=40), 7.4 g of block-copolymer pluronic F127 ($EO_{106}PO_{70}EO_{106}$, mol. wt. 12600) was dissolved in 2 M HCl solution (68.74 g of 35.4% conc. HCl in 315.6 g of distilled water) at 40° C. After 2 hrs of stirring, 28.34 g of tetraethyl orthosilicate was added drop-wise over 30 min and continued stirring for 4 hrs. Then 0.86 g of manganese nitrate (97%, $Mn(NO_3)_2.4H_2O$, mol. wt. 251, Thomas Baker) dissolved in 10 ml of water was added slowly. The stirring was continued for another 20 hrs at 40° C. The gel formed was transferred into a Teflon-lined stainless-steel autoclave. It was heated at 80° C. for 48 hrs. The solid formed was separated by filtration, washed with distilled water (3 L), dried at 100° C. overnight and calcined in air at 550° C. for 8 hrs. Average pore size=21 Å, specific surface area=569 $m^2/g$ and pore wall thickness=82 Å.

Example 2

This example illustrates the preparation of manganese containing three-dimensional, cubic, mesoporous silica catalyst Mn-SBA-16 with Si/Mn molar ratio=30. In a typical synthesis of Mn-SBA-16 (Si/Mn=30), 7.4 g of block-copolymer pluronic F127 ($EO_{106}PO_{70}EC_{106}$, mol. wt. 12600) was dissolved in 2M HCl solution (68.74 g of 35.4% conc. HCl in 315.6 g of distilled water) at 40° C. After 2 hrs of stirring, 28.34 g of tetraethyl orthosilicate was added drop-wise over 30 min and continued stirring for 4 hrs. Then 1.15 g of manganese nitrate (97%, $Mn(NO_3)_2.4H_2O$, mol. wt. 251, Thomas Baker) dissolved in 10 ml of water was added slowly. The stirring was continued for another 20 h at 40° C. The gel formed was transferred into a Teflon-lined stainless-steel autoclave. It was heated at 80° C. for 48 hrs. The solid formed was separated by filtration, washed with distilled water (3 L), dried at 100° C. overnight and calcined in air at 550° C. for 8 hrs. Average pore size=31 Å, specific surface area=585 $m^2/g$ and pore wall thickness=85 Å.

Example 3

This example illustrates the preparation of manganese containing three-dimensional, cubic, mesoporous silica catalyst Mn-SBA-16 with Si/Mn molar ratio=20. In a typical synthesis of Mn-SBA-16 (Si/Mn=20), 7.4 g of block-copolymer pluronic F127 ($EO_{106}PO_{70}EO_{106}$, mol. wt. 12600) was dissolved in 2 M HCl solution (68.74 g of 35.4% conc. HCl in 315.6 g of distilled water) at 40° C. After 2 hrs of stirring, 28.34 g of tetraethyl orthosilicate was added drop-wise over 30 min and continued stirring for 4 hrs. Then 1.72 g of manganese nitrate (97%, $Mn(NO_3)_2.4H_2O$, mol. wt. 251, Thomas Baker) dissolved in 10 ml of water was added slowly. The stirring was continued for another 20 hrs at 40° C. The gel formed was transferred into a Teflon-lined stainless-steel autoclave. It was heated at 80° C. for 48 hrs. The solid formed was separated by filtration, washed with distilled water (3 L), dried at 100° C. overnight and calcined in air at 550° C. for 8 hrs. Average pore size=31 Å, specific surface area=625 $m^2/g$ and pore wall thickness=87 Å.

Example 4

This example illustrates the preparation of manganese containing three-dimensional, cubic, mesoporous silica catalyst Mn-SBA-16 with Si/Mn molar ratio=50. In a typical synthesis of Mn-SBA-16 (Si/Mn=50), 7.4 g of block-copolymer pluronic F127 ($EO_{106}PO_{70}EO_{106}$, mol. wt. 12600) was dissolved in 2 M HCl solution (68.74 g of 35.4% conc. HCl in 315.6 g of distilled water) at 40° C. After 2 hrs of stirring, 28.34 g of tetraethyl orthosilicate was added drop-wise over 30 min and continued stirring for 4 hrs. Then 0.69 g of manganese nitrate (97%, $Mn(NO_3)_{2.4}H_2O$, mol. wt. 251, Thomas Baker) dissolved in 10 ml of water was added slowly. The stirring was continued for another 20 hrs at 40° C. The gel formed was transferred into a Teflon-lined stainless-steel autoclave. It was heated at 80° C. for 48 hrs. The solid formed was separated by filtration, washed with distilled water (3 L), dried at 100° C. overnight and calcined in air at 550° C. for 8 hrs. Average pore size=34 Å, specific surface area=627 $m^2/g$ and pore wall thickness=75 Å.

Example 5

This example illustrates the preparation of manganese-containing three-dimensional, mesoporous, hexagonal silica catalyst, Mn-SBA-12 with Si/Mn molar ratio=20. 8 g of Brij-76 was dissolved, in 40 g of distilled water and 160 g of 0.1 M HCl. The mixture was stirred at 40° C. for 2 hrs. 17.6 g of tetraethyl orthosilicate was added to it over 30 min. Then, 1.07 g of manganese nitrate (97%, $Mn(NO_3)_2.4H_2O$, mol. wt. 251, Thomas Baker) dissolved in 10 ml of water was added slowly and the stirring was continued for 20 hrs. The gel formed was transferred into a Teflon-lined stainless steel autoclave and heated at 100° C. for 24 hrs. The solid formed was recovered by filtration, washed thoroughly with distilled water (3 L), dried at 100° C. for 12 hrs, and calcined at 550° C. for 8 h in the air. Average pore size=32 Å, specific surface area=969 $m^2/g$ and pore wall thickness=74 Å.

Example 6

This example illustrates the preparation of iron-containing three-dimensional hexagonal mesoporous silica catayst Fe-SBA-12 with Si/Fe molar ratio=20. In a typical preparation of Fe-SBA-12 (Si/Fe=20), 8 g of Brij-76 was dissolved in 40 g of distilled water and 160 g of 0.1 M HCl. The mixture was stirred at 40° C. for 2 hrs. 17.6 g of tetraethyl orthosilicate was added to it over 30 min. Then, 0.70 g of anhydrous $FeCl_3$ (96%, mol. wt. 162.21, Merk) dissolved in 10 ml of water was added slowly. The stirring was continued for 20 hrs. The gel formed was transferred into a Teflon-lined stainless steel autoclave and heated at 100° C. for 24 h. The solid formed was recovered by filtration, washed thoroughly with distilled water (3 L), dried at 100° C. for 12 hrs and calcined at 550° C. for 8 hrs in the air. Average pore size=38 Å, specific surface area=982 $m^2/g$ and pore wall thickness=68 Å.

Example 7

This example describes the preparation of vanadium-containing three-dimensional, hexagonal mesoporous silica catalyst V-SBA-12 with Si/V molar ratio=30. In a typical preparation of V-SBA-12 (Si/V=30), 8 g of Brij-76 was dissolved in 40 g of distilled water and 160 g of 2 M HCl. The mixture was stirred at 40° C. for 2 hrs and 17.6 g tetraethyl orthosilicate was added to it over 30 min. Then, 0.33 g of ammonium metavanadate ($NH_4VO_3$, mol. wt. 116.98, 99%, Thomas Baker) was added to the above gel and stirring was continued for 20 h. The gel formed was transferred into a Teflon-lined stainless steel autoclave and heated at 100° C. for 24 hrs. The solid formed was recovered by filtration, washed thoroughly with distilled water (2-3 L), dried at 100° C. for 12 hrs and calcined at 550° C. for 8 hrs in the air. Average pore size=50 Å, specific surface area=576 $m^2/g$ and pore wall thickness=61 Å.

Example 8

This example describes the preparation of manganese containing mesoporous silicate catalyst Mn—Al-SBA-16 with (Si+Al)/Mn molar ratio=30 and Si/Al molar ratio=60. The catalyst was prepared in the same manner as reported in Example 2 except that required quantity of sodium aluminate maintaining Si/Al molar ratio as 20 was added along with tetraethyl orthosilicate. Average pore size=32 Å, specific surface area=592 $m^2/g$ and pore wall thickness=76 Å.

Example 9

This example describes the preparation of benzamide from benzyl amine over the non-precious metal-containing silica catalysts reported in examples 1-8. In a typical reaction, 5 mmol of benzyl amine, 15 mL of 1,4-dioxane and 1 mL of 25% ammonia solution were charged into a stainless-steel pressure reactor. 0.2 g of catalyst was added to it. The reactor was pressurized to 6 bar with air. Temperature of the reactor was raised to 150° C. and the reaction was conducted for 8 hrs while stirring at a speed of 600 revolutions per min. Then, temperature was lowered down to 25° C. and the reactor was depressurized. Catalyst was separated by centrifugation/filtration. Solvent was evaporated and the liquid portion was analyzed by gas chromatography (Varian 3400). Identity of the products was confirmed by comparing with the standard samples.

Catalytic activity data of different metal-containing catalysts in the preparation of amides are listed in Table 1.

TABLE 1

Catalytic activity data of metal-containing solid porous catalysts

| S. No. | Catalyst (Reference example) | Conversion of amine (mol %) | Product selectivity (mol %) | | |
|---|---|---|---|---|---|
| | | | Imine | Amide | Aldehyde |
| 1 | Mn-SBA-16 (Si/Mn = 20) (Eg 3) | 100 | 25.6 | 68.9 | 6.4 |
| 2 | Mn-SBA-16 (Si/Mn = 30) (Eg 2) | 100 | 19.3 | 78.0 | 1.7 |
| 3 | Mn-SBA-16 (Si/Mn = 40) (Eg 1) | 100 | 34.0 | 51.2 | 14.9 |
| 4 | Mn-SBA-16 (Si/Mn = 50) (Eg 4) | 100 | 40.3 | 44.7 | 15.0 |
| 5 | Mn-SBA-12 (Si/Mn = 20) (Eg 5) | 100 | 30.9 | 62.3 | 6.8 |
| 6 | Fe-SBA-12 (Si/Fe = 20) (Eg 6) | 100 | 31.2 | 56.9 | 11.9 |
| 7 | V-SBA-12 (Si/V = 30) (Eg 7) | 100 | 40.9 | 42.5 | 16.6 |
| 8 | Mn—Al-SBA-16 [(Si + Al)/Mn = 30; Si/Al = 60) | 100 | 24.5 | 54.3 | 9.7 (unknown = 11.5) |

Example 10

This example describes the preparation of benzamide from benzyl amine using manganese containing aluminophosphate catalyst (Mn-APO; Al/Mn molar ratio=30) prepared by the method described in a prior art (Logar et al. Microporous Mesoporous Material, Year 2006, Vol. 96, pages 386-395). using $Mn(NO_3)_2$ as Mn source. In a typical reaction, 5 mmol of benzyl amine, 15 mL of tetrahydrofuran and 1 mL of 25% ammonia solution were charged into a stainless-steel pressure reactor. 0.2 g of catalyst was added to it. The reactor was pressurized to 6 bar with air. Temperature of the reactor was raised to 150° C. and the reaction was conducted for 8 hrs while stirring at a speed of 600 revolutions per min. Then, temperature was lowered down to 25° C. and the reactor was depressurized. Catalyst was separated by centrifugation/filtration. Solvent was evaporated and the liquid portion was analyzed by gas chromatography (Variant 3400). Identity of the products was confirmed by comparing with the standard samples. Benzylamine conversion=100 mol % and benzamide selectivity=64 mol % and imine selectivity=21.2 mol %.

Example 11

This example describes the preparation of benzamide from benzyl amine using manganese containing silica aluminophosphate catalyst (Mn-SAPO) prepared by the method described in a prior art (Cheung et al. Microporous Mesoporous Material, Year 2012, Vol. 156, pages 90-96) using $Mn(NO_3)_2$ as Mn source and with Si+Al/Mn molar ratio of 30. In a typical reaction, 5 mmol of benzyl amine, 15 mL of dimethyl sulphoxide and 1 mL of 25% ammonia solution were charged into a stainless-steel pressure reactor. 0.2 g of catalyst was added to it. The reactor was pressurized to 6 bar with oxygen. Temperature of the reactor was raised to 150° C. and the reaction was conducted for 8 hrs while stirring at a speed of 600 revolutions per min. Then, temperature was lowered down to 25° C. and the reactor was depressurized. Catalyst was separated by centrifugation/filtration. Solvent was evaporated and the liquid portion was analyzed by gas chromatography (Varian 3400). Identity of the products was confirmed by comparing with the standard samples. Benzylamine conversion=100 mol %, benzamide selectivity=40.5 mol % and imine selectivity=42.8 mol %).

Example 12

This example describes the preparation of benzamide from benzyl amine over Mn-SBA-16 (Si/Mn=50) catalyst at 130° C. and air pressure of 6 bar. In a typical reaction, 5 mmol of benzyl amine, 15 mL of 1,4-dioxane and 1 mL of 25% ammonia solution were charged into a stainless-steel pressure reactor. 0.2 g of catalyst was added to it. The reactor was pressurized to 6 bar with air. Temperature of the reactor was raised to 130° C and the reaction was conducted for 8 hrs while stirring at a speed of 600 revolutions per min. Then, temperature was lowered down to 25° C. and the reactor was depressurized. Catalyst was separated by centrifugation/filtration. Solvent was evaporated and the liquid portion was analyzed by gas chromatography (Varian 3400). Identity of the products was confirmed by comparing with the standard samples. Benzylamine conversion=90 mol %, benzamide selectivity=73.8 mol %, imine selectivity=14.5 mol % and benzaldehyde=11.7 mol %.

Example 13

This example describes the preparation of benzamide from benzyl amine over Mar SBA-16 (Si/Mn=50) catalyst without using ammonia solution. In a typical reaction, 5 mmol of benzyl amine and 15 mL of 1,4-dioxane were charged into a stainless-steel pressure reactor. 0.2 g of catalyst was added to it. The reactor was pressurized to 6 bar with air. Temperature of the reactor was raised to 150° C. and the reaction was conducted for 8 hrs while stirring at a speed of 600 revolutions per min. Then, temperature was lowered down to 25° C. and the reactor was depressurized. Catalyst was separated by centrifugation/filtration. Solvent was evaporated and the liquid portion was analyzed by gas chromatography (Varian 3400). Identity of the products was confirmed by comparing with the, standard samples. Benzylamine conversion=100 mol %, benzamide selectivity=5.6 mol %. imine selectivity=63.1 mol % and benzaldehyde=31.3 mol %.

Example 14

This example describes the stability and reusability of Mn-SBA-16 (Si/Mn=30) catalyst in the preparation of benzamide from benzyl amine. The catalyst recovered after the catalytic run in Example 9 is washed with methanol, dried at 90° for 4 h and then reused in this experiment. The reaction was conducted in the same manner as described in Example 9 but with the used Mn-SBA-16 (Si/Mn=30) catalyst. This reusability experiment was carried out for three times. 1st Reuse: Benzylamine conversion=100 mol %, benzamide selectivity=78.3 mol %. imine selectivity=19.0 mol % and benzaldehyde=1.7 mol %. $2^{nd}$ Reuse: Benzylamine conversion=100 mol %, benzamide selectivity=77.8 mol %. imine selectivity=19.2 mol % and benzaldehyde=2.0 mol%. $3^{rd}$ Reuse:

Benzylamine conversion=100 mol %, benzamide selectivity=78.0 mol %. imine selectivity=19.1 mol % and benzaldehyde=1.9 mol %.

ADVANTAGES OF THE INVENTION

Advantages of instant invention are as following:
1. Heterogeneous, solid acid catalyst-based process
2. Reusable catalyst process
3. Efficient and eco-friendly process
4. Generates no waste salt by-products.
5. Reaction at moderate conditions and for short periods of time.
6. Applicable to a large number of amines
7. Can be performed in both batch or continuous fixed-bed reaction mode.
8. The novelty in the invention arises from the fact that the reaction has been achieved with excellent conversions using non-precious metals on an ordered mesoporous scaffold. The use of non-precious metals will ensure a more cost effective process while the ordered mesoporous scaffold provides an industrially more feasible platform with better diffusion properties and stability. Previous reports have not been able to show a cost-effective, industrially viable and robust system for carrying out the said reaction.

We claim:

1. A process for producing amide compounds from a primary amine with more than 95% conversion, wherein said process comprises the steps of:
   a. contacting a primary amine, solvent solution with a non-precious metal-containing ordered, mesoporous, solid catalyst, wherein the amount of catalyst ranges from 10 to 40% by weight of amine, said contact being carried out in the optional presence of ammonia solution, solvent ranges from 10 to 30 times by weight of said primary amine and ammonia solution ranges from 2 to 10 times by weight of amine;
   b. pressurizing the reactor with molecular oxygen-containing gas at a pressure of 2 to 6 bar;
   c. subjecting the reaction mixture obtained in step (b) to a temperature in the range of 100 to 160° C. and for a reaction period of 3 to 8 hrs to obtain said amide compound, and,
   d. separating the amide compound from the reaction mixture.

2. The process as claimed in claim 1, wherein in said catalyst the non-precious metal is a third-row transition metal selected from manganese, iron, vanadium, chromium and copper and an ordered, mesoporous solid is selected from the group of mesoporous silicas, silicates, aluminophosphates and silico-aluminophosphate.

3. The process as claimed in claim 1, wherein the ordered, mesoporous catalyst has an average pore size ranging from 25 to 60 Å, pore wall thickness ranging from 40 to 110 Å and specific surface area ranging from 500 to 1000 $m^2/g$.

4. The process as claimed in claim 1, wherein molecular oxygen-containing gas used in step (b) is air or pure oxygen.

5. The process as claimed in claim 1, wherein solvent used in step (a) is selected from the group of 1,4-dioxane, tetrahydrofuran and dimethyl sulphoxide.

6. The process as claimed in claim 1, wherein the process is carried out in the absence of ammonia.

7. The process as claimed in claim 1, wherein the process is carried out in the presence of water.

8. The process as claimed in claim 1, wherein conversion of amine is 100%.

9. The process as claimed in claim 1, wherein the selectivity towards amide compounds is ranging between 42.5 to 78 mol %.

10. The process as claimed in claim 1, wherein imine compounds are formed with a selectivity ranging from 19.2 to 78 mol %.

11. The process as claimed in claim 1 wherein said a non-precious metal-containing ordered, mesoporous, solid catalyst comprises a mesoporous material selected from the group consisting of silica, silicate, aluminophosphate and silico-aluminphosphate mesoporous catalyst or a mixture thereof.

* * * * *